United States Patent
Alsberg et al.

(10) Patent No.: US 11,944,722 B2
(45) Date of Patent: Apr. 2, 2024

(54) HYDROGELS WITH DYNAMICALLY ADJUSTABLE MECHANICAL PROPERTIES

(71) Applicant: CASE WESTERN RESERVE UNIVERSITY, Cleveland, OH (US)

(72) Inventors: Eben Alsberg, Cleveland, OH (US); Oju Jeon, Cleveland, OH (US); Tae-Hee Kim, Cleveland, OH (US)

(73) Assignee: CASE WESTERN RESERVE UNIVERSITY, Cleveland, OH (US)

(*) Notice: Subject to any disclaimer, the term of this patent is extended or adjusted under 35 U.S.C. 154(b) by 0 days.

(21) Appl. No.: 17/474,985

(22) Filed: Sep. 14, 2021

(65) Prior Publication Data

US 2021/0402063 A1  Dec. 30, 2021

Related U.S. Application Data

(63) Continuation of application No. 16/107,774, filed on Aug. 21, 2018, now Pat. No. 11,116,875.

(60) Provisional application No. 62/548,243, filed on Aug. 21, 2017.

(51) Int. Cl.
| | |
|---|---|
| *A61L 24/04* | (2006.01) |
| *A61L 24/00* | (2006.01) |
| *A61L 27/20* | (2006.01) |
| *A61L 27/26* | (2006.01) |
| *A61L 27/36* | (2006.01) |
| *A61L 27/38* | (2006.01) |
| *A61L 27/44* | (2006.01) |
| *A61L 27/52* | (2006.01) |
| *A61L 27/54* | (2006.01) |
| *A61L 27/58* | (2006.01) |
| *C08B 37/00* | (2006.01) |
| *C08G 65/00* | (2006.01) |
| *C08H 1/06* | (2006.01) |
| *C08L 5/04* | (2006.01) |
| *C08L 89/06* | (2006.01) |

(52) U.S. Cl.
CPC .............. *A61L 27/44* (2013.01); *A61L 27/20* (2013.01); *A61L 27/26* (2013.01); *A61L 27/3608* (2013.01); *A61L 27/3834* (2013.01); *A61L 27/52* (2013.01); *A61L 27/54* (2013.01); *A61L 27/58* (2013.01); *C08B 37/0084* (2013.01); *C08G 65/002* (2013.01); *C08H 1/06* (2013.01); *C08L 5/04* (2013.01); *C08L 89/06* (2013.01); *A61L 2300/236* (2013.01); *A61L 2300/252* (2013.01); *A61L 2300/412* (2013.01); *A61L 2300/414* (2013.01); *A61L 2400/16* (2013.01); *A61L 2430/40* (2013.01); *C08L 2205/04* (2013.01); *C08L 2312/00* (2013.01)

(58) Field of Classification Search
CPC .... A61L 27/20; A61L 24/046; A61L 24/0031; A61L 24/0042
See application file for complete search history.

(56) References Cited

U.S. PATENT DOCUMENTS

| | | |
|---|---|---|
| 8,388,948 B2 | 3/2013 | Basu et al. |
| 9,370,606 B2 | 6/2016 | Nakamura et al. |
| 9,642,914 B2 | 5/2017 | Alsberg et al. |
| 2008/0226692 A1 | 9/2008 | Sato et al. |
| 2016/0279868 A1 | 9/2016 | Burdick et al. |
| 2017/0327813 A1 | 11/2017 | Cattolico et al. |

FOREIGN PATENT DOCUMENTS

WO  90/10454 A1  9/1990

OTHER PUBLICATIONS

Rosales et al., Hydrogels with Reversible Mechanics to Probe Dynamic Cell Microenvironments, Angew. Chem. Int. Ed. 2017, 56 12132-12136 (Year: 2017).*
First Named Inventor: Eben Alsberg; U.S. Appl. No. 16/107,708, filed Aug. 21, 2018; NonFinal Office Action, dated Mar. 3, 2022; 17 pgs.
Kadri, R., et al. "Preparation and characterization of nanofunctionalized alginate/methacrylated gelatin hybrid hydrogels." RSC advances 6.33 (2016): 27879-27884.
First Named Inventor: Eben Alsberg; U.S. Appl. No. 16/044,182, filed Jul. 24, 2018; Non-Final Office Action, dated Jun. 24, 2022; 18 pgs.
First Named Inventor: Eben Alsberg; U.S. Appl. No. 16/153,138, filed Oct. 5, 2018; NonFinal Office Action, dated Aug. 12, 2022; 17 pgs.
First Named Inventor: Eben Alsberg; U.S. Appl. No. 12/191,034, filed Aug. 13, 2008; NonFinal Office Action, dated Oct. 4, 2022; 28 pgs.
First Named Inventor: Eben Alsberg; U.S. Appl. No. 16/107,756, filed Aug. 21, 2018; NonFinal Office Action, dated Nov. 17, 2022; 33 pgs.
Gomez, et al. (Carbohydrate Polymers 67 (2007) 296-304) (Year: 2007).
Applicant: Case Western Reserve University, et al.; European Patent Application No. 17879074.7, Filing Date: Dec. 11, 2017; Communication pursuant to Article 94(3) EPC, dated Jul. 20, 2020; 10 pgs.
Chelsea S. Bahney, et al., "Stem Cell-Derived Endochondral Cartilage Stimulates Bone Healing by Tissue Transformation", Journal of Bone and Mineral Research, vol. 29, No. 5, Apr. 22, 2014, pp. 1269-1282.
Chelsea S. Bahney, et al., "The Multifaceted Role of the Vasculature in Endochondral Fracture Repair", Frontiers in Endocrinology, vol. 6, Feb. 5, 2015 (Feb. 5, 2015), p. 4.

(Continued)

*Primary Examiner* — Robert D Harlan
(74) *Attorney, Agent, or Firm* — TAROLLI, SUNDHEIM, COVELL & TUMMINO, LLP (57) ABSTRACT

A composition includes a dual crosslinkable hydrogel that includes a plurality of polymer macromers, which are crosslinked with a first agent and a second agent different than the first agent, wherein the crosslinks formed using the second agent are reversible and repeatable to allow the mechanical properties of the hydrogel to be dynamically adjusted.

12 Claims, 7 Drawing Sheets

(56) References Cited

OTHER PUBLICATIONS

Dazai S, et al., "Leukemia inhibitory factor enhances bone formation in calvarial bone defect", The Journal of Craniofacial Surgery, Nov. 2000, vol. 11, No. 6, Nov. 2000, pp. 513-520.
Guihard P, et al., "Induction of osteogenesis in mesenchymal stem cells by activated monocytes/macrophages depends on Oncostatin M signaling", vol. 50, May 2012.
Italian Patent Office, Document No. 102011902009885A1, (Bionest Ltd), Jul. 1, 2013 (Jul. 1, 2013).
Jeon, et al., "Biochemical and physical signal gradients in hydrogels to control stem cell behavior", Adv Mater. Nov. 26, 2013; 25(44).
Jeon, et al., "In situ forming growth factor-loaded coacervate microparticle-embedded hydrogel for directing encapsulated stem cell fate", Adv Mater. Apr. 2015; 27(13): 2216-2223.
Jeon, et al., "The effect of oxidation on the degradation of photocrosslinkable alginate hydrogels", Biomaterials. May 2012 ; 33(13): 3503-3514.
L. Yang, et al., "Hypertrophic chondrocytes can become osteoblasts and osteocytes in endochondral bone formation", Proceedings of the National Academy of Sciences, vol. 111, No. 33, Aug. 19, 2014, pp. 12097-12102.
Lutolf et al., "Synthetic biomaterials as instructive extracellular microenvironments for morphogenesis in tissue engineering", Nature Biotechnology vol. 23 No. 1 Jan. 2005.
Madl, et al., "Engineering Hydrogel Microenvironments to Recapitulate the Stem Cell Niche", Annu. Rev. Biomed. Eng. 2018. 20:21-47.
Rachelle W. Johnson, et al., "Glycoprotein130 (Gp130)/interleukin-6 (IL-6) signalling in osteoclasts promotes bone formation in periosteal and trabecular bone", BONE, vol. 81, Aug. 7, 2015, pp. 343-351.
Rosales, et al., "Hydrogels with Reversible Mechanics to Probe Dynamic Cell Microenvironments", Angew. Chem. Int. Ed. 2017, 56, 12132-12136.
Rozen, et al., "Fracture repair: Modulation of fracture-callus and mechanical properties by sequential application of IL-6 following PTH 1-34 or PTH 28-48", IL-6 following PTH 1-34 or PTH 28-48, Bone, Pergamon Press., Oxford, GB, vol. 41, No. 3, Aug. 8, 2007, pp. 437-445.
Shih, et al., "Tuning stiffness of cell-laden hydrogel via host-guest interactions", . Mater. Chem. B, 2016, 4969-4974.
Tamura, et al., "Click-crosslinkable and photodegradable gelatin hydrogels for cytocompatible optical cell manipulation in natural environment", Scientific Reports, UK, 2015.
Xin Zhou, et al., "Chondrocytes Transdifferentiate into Osteoblasts in Endochondral Bone during Development, Postnatal Growth and Fracture Healing in Mice", PLOS Genetics, vol. 10, No. 12, Dec. 4, 2014.
First Named Inventor: Eben Alsberg; U.S. Appl. No. 16/107,756, filed Aug. 21, 2018; NonFinal Office Action, dated Aug. 26, 2020; 16 pgs.
First Named Inventor: Eben Alsberg; U.S. Appl. No. 16/726,375, filed Dec. 24, 2019; NonFinal Office Action, dated Oct. 5, 2020.
Applicant: Case Western Reserve University; PCT International Application No. PCT/US19/26678; International Filing Date: Apr. 9, 2019; PCT International Search Report and Written Opinion; Authorized Officer: Lee W. Young; Date of Completion: Jun. 11, 2019; 11 pgs.
First Named Inventor: Eben Alsberg; U.S. Appl. No. 17/544,544, filed Dec. 7, 2021; NonFinal Office Action, dated Dec. 8, 2022; 6 pgs.

* cited by examiner

HYDROGELS WITH DYNAMICALLY ADJUSTABLE MECHANICAL PROPERTIES

RELATED APPLICATION

This application claims priority from U.S. Provisional Application No. 62/548,243, filed Aug. 21, 2017, the subject matter of which is incorporated herein by reference in its entirety.

GOVERNMENT FUNDING

This invention was made with government support under Grant Nos. R01AR069564 and R01AR066193 awarded by The National Institutes of Health. The United States government has certain rights to the invention.

BACKGROUND

The ability to engineer biomaterials that can control cell behaviors through dynamic mechanics of biomaterials may extend the capabilities and potentials in engineering tissue substitutes from stem cells. Recently, stiffness of cell-laden hydrogels could be decreased or increased through matrix degradation or secondary crosslinking on the cell-laden hydrogel networks. However, changes in matrix mechanics are irreversible in these studies, hence the aforementioned strategies might not be ideal for understanding the influence of dynamic mechanics on cellular mechanosensing. Since the extracellular matrix (ECM) is highly dynamic during tissue development or regeneration, biomaterial systems with reversibly tunable matrix stiffness are highly desirable in tissue engineering and regenerative medicine.

Several strategies have been developed to reversibly control hydrogel stiffness. A reversibly tunable hydrogel system using adamantane-functionalized multi-arm PEG and a β-cyclodextrin (βCD)-modified PVA base on reversible guest-host interactions between adamantane and βCD has been shown. However, this system exhibited a limited tunability in stiffness (from approximately 2 to 3.5 kPa). A hyaluronic acid hydrogel system with reversible mechanics by sequential photo-degradation and photocrosslinking to soften and then stiffen their hydrogel to apply dynamic mechanical signaling for human mesenchymal stem cells (hMSCs) over a wider range of moduli (from approximately 3 to 30 kPa) has also been shown. However, hMSCs were cultured on a two-dimensional (2D) surface, and the number of softening-stiffening cycles was limited. While 3D systems represent more biomimetic microenvironments, this system may fail to provide an accurate representation of a physiological cellular microenvironment as it lacks the 3D signals found in native tissue.

SUMMARY

Embodiments described herein relate to hydrogels having repeatable and reversible dynamically adjustable mechanical properties, methods of forming the hydrogels, and to their use in regenerative medicine, cell-based technologies, drug delivery, and tissue engineering applications. For example, compositions containing hydrogels described herein can be used as building blocks for tissue engineering as well as for functional implantable objects for cell therapy applications. The hydrogel can optionally include a plurality of cells dispersed therein and be cytocompatible, and, upon degradation, produce substantially non-toxic products. Advantageously, the effect of reversible mechanical signals to cells encapsulated in the hydrogels can increase and decrease cells spreading to recapitulate multifaceted and intricate developmental and regenerative processes to drive the engineering of complex tissues.

In some embodiments, the dynamically adjustable hydrogel can be substantially cytocompatible (i.e., substantially non-cytotoxic) and include controllable physical properties, such as degradation rate, swelling behavior, and mechanical properties. In some embodiments, the dynamically adjustable hydrogel can be a dual crosslinkable hydrogel that includes a plurality of polymer macromers that are crosslinked with a first agent and a second agent different than the first agent. The crosslinks formed using the second agent are reversible and repeatable to allow the mechanical properties of the hydrogel to be dynamically adjusted.

In some embodiments, the stiffness of the hydrogel is dynamically adjusted by increasing or decreasing crosslinking with the second agent. An increase of the crosslinks formed using the second agent increases the stiffness of the hydrogel and a decrease in the crosslinks decreases the stiffness of the hydrogel.

In other embodiments, the dynamically adjustable hydrogel can include at least one bioactive agent. The release of the bioactive agent from the hydrogel can be controlled by dynamically adjusting the mechanical properties of the hydrogel.

In some embodiment, the dynamically adjustable hydrogel can include a plurality of cells dispersed on and/or within the hydrogel. The growth and/or proliferation of the cells within the hydrogel can be controlled by dynamically adjusting the mechanical properties of the hydrogel.

In some embodiments, the polymer macromers can include biodegradable acrylated and/or methacrylated natural polymer macromers. The acrylated and/or methacrylated, natural polymer macromers can be polysaccharides, which are optionally oxidized, such as oxidized, acrylated and/or methacrylated alginates.

In some embodiments, the polymer macromers can be photocrosslinkable with the first agent and be ionically crosslinkable with the second agent, such as calcium ions.

Other embodiments described herein relate to a method of modulating the mechanical properties of a hydrogel. The method can include dynamically adjusting crosslinking of a dual crosslinkable hydrogel that includes a plurality of polymer macromers that are crosslinked with a first agent and a second agent different than the first agent. The crosslinks formed using the second agent can be reversible and repeatable to allow the mechanical properties of the hydrogel to be dynamically adjusted.

Still other embodiments relate to a method of regulating cell behavior. The method can include providing a dual crosslinkable hydrogel that includes a plurality of polymer macromers, which are crosslinked with a first agent and a second agent different than the first agent, a plurality of cells dispersed in the crosslinked polymer macromers, and optionally at least one bioactive agent dispersed in the polymer macromers. The crosslinks formed using the second agent can be reversible and repeatable to allow the mechanical properties of the hydrogel to be dynamically adjusted. The mechanical properties of the dual crosslinkable hydrogel can be dynamically adjusted to modulate the growth and/or proliferation of the cells within the hydrogel. Optionally, the release of the bioactive agent from the hydrogel can also be controlled by dynamically adjusting the mechanical properties of the hydrogel.

DETAILED DESCRIPTION

Methods involving conventional molecular biology techniques are described herein. Such techniques are generally known in the art and are described in detail in methodology treatises, such as *Current Protocols in Molecular Biology*, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., *Glossary of Genetics: Classical and Molecular*, 5th Ed., Springer-Verlag: New York, 1991, and Lewin, *Genes V*, Oxford University Press: New York, 1994. The definitions provided herein are to facilitate understanding of certain terms used frequently herein and are not meant to limit the scope of the present invention.

In the context of the present invention, the term "bioactive agent" can refer to any agent capable of promoting tissue growth, inhibition, formation, destruction, and/or targeting a specific disease state. Examples of bioactive agents can include, but are not limited to, chemotactic agents, various proteins (e.g., short term peptides, bone morphogenic proteins, collagen, glycoproteins, and lipoprotein), cell attachment mediators, biologically active ligands, integrin binding sequence, various growth and/or differentiation agents and fragments thereof (e.g., epidermal growth factor (EGF), hepatocyte growth factor (HGF), vascular endothelial growth factors (VEGF), fibroblast growth factors (e.g., bFGF), platelet derived growth factors (PDGF), insulin-like growth factor (e.g., IGF-I, IGF-II) and transforming growth factors (e.g., TGF-β I-III), parathyroid hormone, parathyroid hormone related peptide, bone morphogenic proteins (e.g., BMP-2, BMP-4, BMP-6, BMP-7, BMP-12, BMP-13, BMP-14), transcription factors, such as sonic hedgehog, growth differentiation factors (e.g., GDF5, GDF6, GDF8), recombinant human growth factors (e.g., MP52 and the MP-52 variant rhGDF-5), cartilage-derived morphogenic proteins (CDMP-1, CDMP-2, CDMP-3), small molecules that affect the upregulation of specific growth factors, DNA fragments, DNA plasmids, MMPs, TIMPs, interfering RNA molecules, such as siRNAs, oligonucleotides, proteoglycans, glycoproteins, glycosaminoglycans, and DNA encoding for shRNA.

As used herein, the terms "biodegradable" and "bioresorbable" may be used interchangeably and refer to the ability of a material (e.g., a natural polymer or macromer) to be fully resorbed in vivo. "Full" can mean that no significant extracellular fragments remain. The resorption process can involve elimination of the original implant material(s) through the action of body fluids, enzymes, cells, and the like.

As used herein, the term "function and/or characteristic of a cell" can refer to the modulation, growth, and/or proliferation of at least one cell, such as a progenitor cell and/or differentiated cell, the modulation of the state of differentiation of at least one cell, and/or the induction of a pathway in at least one cell, which directs the cell to grow, proliferate, and/or differentiate along a desired pathway, e.g., leading to a desired cell phenotype, cell migration, angiogenesis, apoptosis, etc.

The term "gel" includes gels and hydrogels.

As used herein, the term "macromer" can refer to any natural polymer or oligomer.

As used herein, the term "polynucleotide" can refer to oligonucleotides, nucleotides, or to a fragment of any of these, to DNA or RNA (e.g., mRNA, rRNA, siRNA, tRNA) of genomic or synthetic origin which may be single-stranded or double-stranded and may represent a sense or antisense strand, to peptide nucleic acids, or to any DNA-like or RNA-like material, natural or synthetic in origin, including, e.g., iRNA, ribonucleoproteins (e.g., iRNPs). The term can also encompass nucleic acids (i.e., oligonucleotides) containing known analogues of natural nucleotides, as well as nucleic acid-like structures with synthetic backbones.

As used herein, the term "polypeptide" can refer to an oligopeptide, peptide, polypeptide, or protein sequence, or to a fragment, portion, or subunit of any of these, and to naturally occurring or synthetic molecules. The term "polypeptide" can also include amino acids joined to each other by peptide bonds or modified peptide bonds, i.e., peptide isosteres, and may contain any type of modified amino acids. The term "polypeptide" can also include peptides and polypeptide fragments, motifs and the like, glycosylated polypeptides, and all "mimetic" and "peptidomimetic" polypeptide forms.

As used herein, the term "cell" can refer to any progenitor cell, such as totipotent stem cells, pluripotent stem cells, and multipotent stem cells, as well as any of their lineage descendant cells, including more differentiated cells. The terms "stem cell" and "progenitor cell" are used interchangeably herein. The cells can derive from embryonic, fetal, or adult tissues. Examples of progenitor cells can include totipotent stem cells, multipotent stem cells, mesenchymal stem cells (MSCs), neuronal stem cells, hematopoietic stem cells, pancreatic stem cells, cardiac stem cells, embryonic stem cells, embryonic germ cells, neural crest stem cells, kidney stem cells, hepatic stem cells, lung stem cells, hemangioblast cells, and endothelial progenitor cells. Additional exemplary progenitor cells can include de-differentiated chondrogenic cells, chondrogenic cells, cord blood stem cells, multi-potent adult progenitor cells, myogenic cells, osteogenic cells, tendogenic cells, ligamentogenic cells, adipogenic cells, and dermatogenic cells.

As used herein, the term "subject" can refer to any animal, including, but not limited to, humans and non-human animals (e.g., rodents, arthropods, insects, fish (e.g., zebrafish)), non-human primates, ovines, bovines, ruminants, lagomorphs, porcines, caprines, equines, canines, felines, ayes, etc.), which is to be the recipient of a particular treatment. Typically, the terms "patient" and "subject" are used interchangeably herein in reference to a human subject.

As used herein, the term "tissue" can refer to an aggregate of cells having substantially the same function and/or form in a multicellular organism. "Tissue" is typically an aggregate of cells of the same origin, but may be an aggregate of cells of different origins. The cells can have the substantially same or substantially different function, and may be of the same or different type. "Tissue" can include, but is not limited to, an organ, a part of an organ, bone, cartilage, skin, neuron, axon, blood vessel, cornea, muscle, fascia, brain, prostate, breast, endometrium, lung, pancreas, small intestine, blood, liver, testes, ovaries, cervix, colon, stomach, esophagus, spleen, lymph node, bone marrow, kidney, peripheral blood, embryonic, or ascite tissue.

As used herein, the terms "inhibit," "silencing," and "attenuating" can refer to a measurable reduction in expression of a target mRNA (or the corresponding polypeptide or protein) as compared with the expression of the target mRNA (or the corresponding polypeptide or protein) in the absence of an interfering RNA molecule of the present invention. The reduction in expression of the target mRNA (or the corresponding polypeptide or protein) is commonly referred to as "knock-down" and is reported relative to levels present following administration or expression of a non-targeting control RNA.

As used herein, the term "population" can refer to a collection of cells, such as a collection of progenitor and/or differentiated cells.

As used herein, the term "differentiated" as it relates to the cells can refer to cells that have developed to a point where they are programmed to develop into a specific type of cell and/or lineage of cells. Similarly, "non-differentiated" or "undifferentiated" as it relates to the cells can refer to progenitor cells, i.e., cells having the capacity to develop into various types of cells within a specified lineage.

Embodiments described herein relate to hydrogels having repeatable and reversible dynamically adjustable mechanical properties, methods of forming the hydrogels, and to their use in regenerative medicine, cell-based technologies, drug delivery, and tissue engineering applications. For example, compositions containing hydrogels described herein can be used as building blocks for tissue engineering as well as for functional implantable objects for cell therapy applications. The hydrogel can optionally include a plurality of cells dispersed therein and be cytocompatible, and, upon degradation, produce substantially non-toxic products. Advantageously, the effect of reversible mechanical signals cell encapsulated in the hydrogels can increase and decrease cell spreading and proliferation to recapitulate multifaceted and intricate developmental and regenerative processes to drive the engineering of complex tissues.

The dynamically adjustable hydrogel can be substantially cytocompatible (i.e., substantially non-cytotoxic) and include controllable physical properties, such as degradation rate, swelling behavior, and mechanical properties. In some embodiments, the dynamically adjustable hydrogel can be a dual crosslinkable hydrogel that includes a plurality of dual crosslinkable polymer macromers that are crosslinked with a first agent and a second agent different than the first agent. The crosslinks formed using the second agent (i.e., the second crosslinks or secondary crosslinking network) can be reversible and repeatable to allow the mechanical properties of the hydrogel to be dynamically adjusted.

The polymer macromers that are crosslinked with a first agent and a second agent different than the first agent can include any dual crosslinkable hydrogel forming polymer macromers, such as natural polymer macromers (e.g., collagen and alginate) and synthetic polymer macromers (e.g., poly(vinyl alcohol), poly(ethylene glycol), and poly(acrylic acid). In some embodiments, the dual crosslinkable hydrogel forming polymer macromers can be natural polymer macromers, which can be potentially be crosslinked by actinic radiation (e.g., photocrosslinkable) or crosslinkable using other means (e.g., chemical, thermal, acoustic, magnetic, etc.)

In some embodiments, the natural polymer macromers can include any crosslinkable natural polymer or oligomer that includes a functional group (e.g., an acrylate group and/or methacrylate group) and that can be further polymerized. Examples of natural polymers or oligomers are saccharides (e.g., mono-, di-, oligo-, and poly-saccharides), such as glucose, galactose, fructose, lactose and sucrose, collagen, gelatin, glycosaminoglycans, poly(hyaluronic acid), poly(sodium alginate), hyaluronan, alginate, heparin and agarose.

In some embodiments, the natural polymer macromers can include acrylated and/or methacrylated natural polymer macromers. Acrylated and/or methacrylated natural polymer macromers can include saccharides (e.g., mono-, di-, oligo-, and poly-saccharides), such as glucose, galactose, fructose, lactose and sucrose, collagen, gelatin, glycosaminoglycans, poly(hyaluronic acid), poly(sodium alginate), hyaluronan, alginate, heparin and agarose that can be readily oxidized to form free aldehyde units.

In some embodiments, the acrylated or methacrylated, natural polymer macromers are polysaccharides, which are optionally oxidized so that up to about 50% of the saccharide units therein are converted to aldehyde saccharide units. Control over the degree of oxidation of the natural polymer macromers permits regulation of the gelling time used to form the hydrogel as well as the mechanical properties, which allows for tailoring of these mechanical properties depending on the clinical application.

In other embodiments, acrylated and/or methacrylated, natural polymer macromers can include oxidized, acrylated or methacrylated, alginates, which are optionally oxidized so that up to about 50% of the saccharide units therein are converted to aldehyde saccharide units. Natural source alginates, for example, from seaweed or bacteria, are useful and can be selected to provide side chains with appropriate M (mannuronate) and G (guluronate) units for the ultimate use of the polymer. Alginate materials can be selected with high guluronate content since the guluronate units, as opposed to the mannuronate units, more readily provide sites for oxidation and crosslinking. Isolation of alginate chains from natural sources can be conducted by conventional methods. See Biomaterials: Novel Materials from Biological Sources, ed. Byrum, Alginates chapter (ed. Sutherland), p. 309-331 (1991). Alternatively, synthetically prepared alginates having a selected M and G unit proportion and distribution prepared by synthetic routes, such as those analogous to methods known in the art, can be used. Further, either natural or synthetic source alginates may be modified to provide M and G units with a modified structure. The M and/or G units may also be modified, for example, with polyalkylene oxide units of varied molecular weight such as shown for modification of polysaccharides in Spaltro (U.S. Pat. No. 5,490,978) with other alcohols such as glycols. Such modification generally will make the polymer more soluble, which generally will result in a less viscous material. Such modifying groups can also enhance the stability of the polymer. Further, modification to provide alkali resistance, for example, as shown by U.S. Pat. No. 2,536,893, can be conducted.

The oxidation of the natural polymer macromers (e.g., alginate material) can be performed using a periodate oxidation agent, such as sodium periodate, to provide at least some of the saccharide units of the natural polymer macromer with aldehyde groups. The degree of oxidation is controllable by the mole equivalent of oxidation agent, e.g., periodate, to saccharide unit. For example, using sodium periodate in an equivalent % of from 2% to 100%, preferably 1% to 50%, a resulting degree of oxidation, i.e., % if saccharide units converted to aldehyde saccharide units, from about 2% to 50% can be obtained. The aldehyde groups provide functional sites for crosslinking and for bonding tissue, cells, prosthetics, grafts, and other material that is desired to be adhered. Further, oxidation of the natural polymer macromer facilitates their degradation in vivo, even if they are not lowered in molecular weight. Thus, high molecular weight alginates, e.g., of up to 300,000 daltons, may be degradeable in vivo, when sufficiently oxidized, i.e., preferably at least 5% of the saccharide units are oxidized.

In some embodiments, the natural polymer macromer (e.g., alginate) can be acrylated or methacrylated by reacting an acryl group or methacryl with a natural polymer or oligomer to form the oxidized, acrylated or methacrylated natural polymer macromer (e.g., alginate). For example, oxidized alginate can be dissolved in a solution chemically functionalized with N-hydroxysuccinimide and 1-ethyl-3-(3-dimethylaminopropyl)-carbodiimide hydrochloride to activate the carboxylic acids of alginate and then reacted with 2-aminoethylmethacrylate to provide a plurality of methacrylate groups on the alginate.

The degree of acrylation or methacrylation can be controlled to control the degree of subsequent crosslinking of the acrylate and methacrylates as well as the mechanical properties, and biodegradation rate of the composition. The degree of acrylation or methacrylation can be about 1% to about 50%, although this ratio can vary more or less depending on the end use of the composition.

In some embodiments, a solution of natural polymer macromers can be crosslinked with a first agent to form hydrogel having mechanical properties that can be dynamically adjusted by reversible and repeatable crosslinking the hydrogel with a second agent. The mechanical properties that can be adjusted include, for example, stiffness, Young's modulus, tensile strength, viscosity, resistance to shear or tensile loading and excessive swelling, as well as biodegradation rate.

In some embodiments, the first agent can crosslink acrylate and/or methacrylate groups of the acrylated or methacrylated natural polymer macromer to form a plurality of first crosslinking networks. The first crosslinking networks formed by crosslinking the acrylate groups or methacrylate groups of the acrylated and/or methacrylated natural polymer macromer can provide the first mechanical properties, such as stiffness, to the hydrogel, which can be dynamically adjusted by reversible and repeatable crosslinking the hydrogel with a second agent. For example, the stiffness of the hydrogels can be reversibly and repeatably adjusted by increasing or decreasing secondary crosslinking with the second agent.

In some embodiments, the acrylate or methacrylate groups of the acrylated and/or methacrylated natural polymer macromer can be crosslinked by photocrosslinking using UV light in the presence of photoinitiators. For example, acrylated and/or methacrylated natural polymer macromers can be photocrosslinked in an appropriate amount of $diH_2O$ or aqueous media (e.g., PBS) containing a desired amount of a photoinitiator.

The acrylated and/or methacrylated natural polymer macromers can be exposed to a light source at a wavelength and for a time to promote crosslinking of the acrylate groups of the macromers and form the photocrosslinked biodegradable hydrogel.

A photoinitiator can include any photo-initiator that can initiate or induce polymerization of the acrylate or methacrylate macromer. Examples of the photoinitiator can include camphorquinone, benzoin methyl ether, 2-hydroxy-2-methyl-1-phenyl-1-propanone, diphenyl(2,4,6-trimethylbenzoyl)phosphine oxide, benzoin ethyl ether, benzophenone, 9,10-anthraquinone, ethyl-4-N,N-dimethylaminobenzoate, diphenyliodonium chloride and derivatives thereof.

The hydrogel formed by crosslinking, the polymer macromers with the first agent can be reversibly and repeatably crosslinked with the second agent to dynamically adjust the mechanical properties of the hydrogel. For example, the stiffness of the hydrogels can be reversibly and repeatably adjusted by increasing or decreasing crosslinking with the second agent. In some embodiment, an increase of the crosslinks formed using the second agent increases the stiffness of the hydrogel and a decrease in the crosslinks decreases the stiffness of the hydrogel.

In some embodiments, a second crosslink network of reversible crosslinks can be formed by ionically crosslinking the single crosslinked hydrogel formed from the natural polymer macromers. For example gluronic acids of different alginates in single crosslinked alginate hydrogel can form ionic crosslinks with $Ca^{2+}$ provide by an aqueous solution of $CaCl_2$ resulting in a dual crosslinked hydrogel network. As the concentration of the ionic crosslinker (e.g., $Ca^{2+}$) in the hydrogel increases the secondary crosslinking and elastic moduli increase resulting in an increase in stiffness of the hydrogel. Subsequent decrease in the concentration of the ionic crosslinker by, for example, incubation of the hydrogel in a buffer solution decreases the ionic crosslinking and the elastic moduli of the hydrogel resulting in softening of the hydrogel.

In some embodiment, the dynamically adjustable hydrogel can include a plurality of cells dispersed on and/or within the hydrogel. Advantageously, the growth and/or proliferation of the cells within the hydrogel can be controlled by dynamically adjusting the mechanical properties of the hydrogel. For example, the proliferation rate of cells encapsulated in soft hydrogels decreased when the hydrogels were stiffened. Conversely, when stiffened hydrogels were softened again, by, for example, removing or reducing the concentration of an ion crosslinker, the decreased proliferation rate of the encapsulated cells recovered.

The cells provided in the hydrogel can be autologous, xenogeneic, allogeneic, and/or syngeneic. Where the cells are not autologous, it may be desirable to administer immunosuppressive agents in order to minimize immunorejection. The cells employed may be primary cells, expanded cells, or cell lines, and may be dividing or non-dividing cells. Cells may be expanded ex vivo prior to introduction into or onto the hydrogel. For example, autologous cells can be expanded in this manner if a sufficient number of viable cells cannot be harvested from the host subject. Alternatively or additionally, the cells may be pieces of tissue, including tissue that has some internal structure. The cells may be primary tissue explants and preparations thereof, cell lines (including transformed cells), or host cells.

Generally, cells can be introduced into the hydrogels in vitro, although in vivo seeding approaches can optionally or additionally be employed. Cells may be mixed with the macromers used to form the hydrogels and cultured in an adequate growth (or storage) medium to ensure cell viability. If the hydrogel is to be implanted for use in vivo after in vitro seeding, for example, sufficient growth medium may be supplied to ensure cell viability during in vitro culture prior to in vivo application. Once the hydrogels has been implanted, the nutritional requirements of the cells can be met by the circulating fluids of the host subject.

Any available method may be employed to introduce the cells into the hydrogels. For example, cells may be injected into the hydrogels (e.g., in combination with growth medium) or may be introduced by other means, such as pressure, vacuum, osmosis, or manual mixing. Alternatively or additionally, cells may be layered on the hydrogels, or the hydrogels may be dipped into a cell suspension and allowed to remain there under conditions and for a time sufficient for the cells to incorporate within or attach to the hydrogel. Generally, it is desirable to avoid excessive manual manipulation of the cells in order to minimize cell death during the impregnation procedure. For example, in some situations it may not be desirable to manually mix or knead the cells with the hydrogels; however, such an approach may be useful in those cases in which a sufficient number of cells will survive the procedure. Cells can also be introduced into the hydrogels in vivo simply by placing the hydrogel in the subject adjacent a source of desired cells.

As those of ordinary skill in the art will appreciate, the number of cells to be introduced into the hydrogels will vary based on the intended application of the hydrogel and on the type of cell used. Where dividing autologous cells are being introduced by injection or mixing into the hydrogel, for example, a lower number of cells can be used. Alternatively, where non-dividing cells are being introduced by injection or mixing into the hydrogel, a larger number of cells may be required. It should also be appreciated that the hydrogel can be in either a hydrated or lyophilized state prior to the addition of cells. For example, the hydrogel can be in a lyophilized state before the addition of cells is done to re-hydrate and populate the scaffold with cells.

In other embodiments, the hydrogels can include at least one attachment molecule to facilitate attachment of at least one cell thereto. The attachment molecule can include a polypeptide or small molecule, for example, and may be chemically immobilized onto the hydrogel to facilitate cell attachment. Examples of attachment molecules can include fibronectin or a portion thereof, collagen or a portion thereof, polypeptides or proteins containing a peptide attachment sequence (e.g., arginine-glycine-aspartate sequence) (or other attachment sequence), enzymatically degradable peptide linkages, cell adhesion ligands, growth factors, degradable amino acid sequences, and/or protein-sequestering peptide sequences.

In other embodiments, the dynamically adjustable hydrogel can include at least one bioactive agent. Advantageously, the release of the bioactive agent from the hydrogel can be controlled by dynamically adjusting the mechanical properties of the hydrogel. The at least one bioactive agent can include any agent capable of modulating a function and/or characteristic of a cell that is dispersed on or within the hydrogel. Alternatively or additionally, the bioactive agent may be capable of modulating a function and/or characteristic of an endogenous cell surrounding the hydrogel implanted in a tissue defect, for example, and guide the cell into the defect.

Examples of bioactive agents include chemotactic agents, various proteins (e.g., short term peptides, bone morphogenic proteins, collagen, glycoproteins, and lipoprotein), cell attachment mediators, biologically active ligands, integrin binding sequence, various growth and/or differentiation agents and fragments thereof (e.g., EGF), HGF, VEGF, fibroblast growth factors (e.g., bFGF), PDGF, insulin-like growth factor (e.g., IGF-I, IGF-II) and transforming growth factors (e.g., TGF-β I-III), parathyroid hormone, parathyroid hormone related peptide, bone morphogenic proteins (e.g., BMP-2, BMP-4, BMP-6, BMP-7, BMP-12, BMP-13, BMP-14), sonic hedgehog, growth differentiation factors (e.g., GDF5, GDF6, GDF8), recombinant human growth factors (e.g., MP-52 and the MP-52 variant rhGDF-5), cartilage-derived morphogenic proteins (CDMP-1, CDMP-2, CDMP-3), small molecules that affect the upregulation of specific growth factors, polynucleotides, DNA fragments, DNA plasmids, MMPs, TIMPs, interfering RNA molecules, such as siRNAs, DNA encoding for an shRNA of interest, oligonucleotides, proteoglycans, glycoproteins, and glycosaminoglycans.

Other embodiments described herein relate to a method of regulating cell behavior. The method can include providing a dual crosslinkable hydrogel that includes a plurality of polymer macromers that are crosslinked with a first agent and a second agent different than the first agent and a plurality of cells dispersed in the crosslinked polymer macromers. The crosslinks formed using the second agent can be reversible and repeatable to allow the mechanical properties of the hydrogel to be dynamically adjusted. The mechanical properties of the dual crosslinkable hydrogel can be dynamically adjusted to modulate the growth and/or proliferation of the cells within the hydrogel.

By way of example, hMSCs encapsulated in the static stiff (ST) hydrogels that were ionically crosslinked displayed a rounded morphology for 4 weeks. In contrast, hMSCs encapsulated in the static soft (SO) hydrogels, which were not ionically crosslinked, demonstrated cell spreading at the $1^{st}$ week and continuously spread for 4 weeks. When the soft hydrogel constructs were stiffened at the $1^{st}$ week and cultured for another week (SO-ST), the morphology of hMSCs was rounded, though the hMSC spread was much greater than in the static SO hydrogels. The rounded morphology of hMSCs in the stiffened hydrogels (SO-ST) changed significantly in the $3^{rd}$ week to a spread morphology in response to softening hydrogels at the $2^{nd}$ week (SO-ST-SO). Similar to the morphology changes of the hMSCs in the $2^{nd}$ week, the spread morphology of the hMSCs in the softened hydrogels rounded again by stiffening the hydrogel constructs (SO-ST-SO-ST). When the Stiff hydrogel constructs were softened at the $1^{st}$ week and cultured for another week (ST-SO), the hMSCs started spreading, whereas the hMSCs remained rounded in the static Stiff hydrogel constructs. The spread morphology of the hMSCs in the softened hydrogels (ST-SO) changed to a rounded morphology in the $3^{rd}$ week by stiffening the hydrogel constructs (ST-SO-ST). This rounded morphology of the hMSCs in the stiffened hydrogel constructs could be also changed to a spread morphology by softening the hydrogel constructs (ST-SO-ST-SO). Moreover, as the stiffness of the hydrogel constructs was decreased, cell area increased. Upon stiffening the hydrogel constructs, cell area decreased again.

hMSCs encapsulated in static hydrogels continuously grew for 4 weeks as determined by a DNA content assay while the proliferation rate of hMSCs encapsulated in the static SO hydrogels (SO-SO-SO-SO) was significantly higher than that of hMSCs in static ST hydrogels (ST-ST-ST-ST). The proliferation rate of hMSCs encapsulated in the Soft hydrogels decreased when the hydrogel constructs were stiffened at the $1^{st}$ week (SO-ST-SO-ST). When the stiffened hydrogel constructs were softened again by removing $Ca^{2+}$ the $2^{nd}$ week, the decreased proliferation rate of the encapsulated hMSCs recovered. Similar to the SO hydrogel constructs, the proliferation rate of hMSCs encapsulated in the ST hydrogels could increase by softening the hydrogel constructs by the softening at 1st week (ST-SO-ST-SO). Subsequent hydrogel constructs stiffening decreased this increased proliferation rate of encapsulated hMSCs. These results demonstrated that the growth of encapsulated hMSCs was reversibly and repeatedly controllable by stiffening or softening the hydrogel constructs.

The dynamically adjustable hydrogel can be used in a variety of biomedical applications, including tissue engineering, drug delivery applications, and regenerative medicine. In one example, dynamically adjustable hydrogel can be used to promote tissue growth in a subject. One step of the method can include identifying a target site. The target site can comprise a tissue defect (e.g., cartilage and/or bone defect) in which promotion of new tissue (e.g., cartilage and/or bone) is desired. The target site can also comprise a diseased location (e.g., tumor). Methods for identifying tissue defects and disease locations are known in the art and can include, for example, various imaging modalities, such as CT, MRI, and X-ray.

The tissue defect can include a defect caused by the destruction of bone or cartilage. For example, one type of cartilage defect can include a joint surface defect. Joint surface defects can be the result of a physical injury to one or more joints or, alternatively, a result of genetic or environmental factors. Most frequently, but not exclusively, such a defect will occur in the knee and will be caused by trauma, ligamentous instability, malalignment of the extremity, meniscectomy, failed aci or mosaicplasty procedures, primary osteochondritis dessecans, osteoarthritis (early osteoarthritis or unicompartimental osteochondral defects), or tissue removal (e.g., due to cancer). Examples of bone defects can include any structural and/or functional skeletal abnormalities. Non-limiting examples of bone defects can include those associated with vertebral body or disc injury/destruction, spinal fusion, injured meniscus, avascular necrosis, cranio-facial repair/reconstruction (including dental repair/reconstruction), osteoarthritis, osteosclerosis, osteoporosis, implant fixation, trauma, and other inheritable or acquired bone disorders and diseases.

Tissue defects can also include cartilage defects. Where a tissue defect comprises a cartilage defect, the cartilage defect may also be referred to as an osteochondral defect when there is damage to articular cartilage and underlying (subchondral) bone. Usually, osteochondral defects appear on specific weight-bearing spots at the ends of the thighbone, shinbone, and the back of the kneecap. Cartilage defects in the context of the present invention should also be understood to comprise those conditions where surgical repair of cartilage is required, such as cosmetic surgery (e.g., nose, ear). Thus, cartilage defects can occur anywhere in the body where cartilage formation is disrupted, where cartilage is damaged or non-existent due to a genetic defect, where cartilage is important for the structure or functioning of an organ (e.g., structures such as menisci, the ear, the nose, the larynx, the trachea, the bronchi, structures of the heart valves, part of the costae, synchondroses, enthuses, etc.), and/or where cartilage is removed due to cancer, for example.

After identifying a target site, such as a cranio-facial cartilage defect of the nose, the dynamically adjustable hydrogel can be administered to the target site. The hydrogel can be prepared by mixing a plurality of cells, such as chondrocytes, with a plurality of methacrylated alginate macromers to form a solution. Chondrocytes may be obtained from a host subject and then expanded to a desired density ex vivo. The solution can then be photocrosslinked and subsequently ionically crosslinked. The ionic crosslinking can be dynamically adjusted to modulate mechanical properties of the hydrogel and hence the growth and/or proliferation of the cells.

Next, the dynamically adjustable hydrogel may be loaded into a syringe or other similar device and injected or implanted into the tissue defect. Upon injection or implantation into the tissue defect, the hydrogel be formed into the shape of the tissue defect using tactile means.

After implanting the dynamically adjustable hydrogel into the subject, the chondrocytes can begin to migrate from the hydrogel into the tissue defect, express growth and/or differentiation factors, and/or promote chondroprogenitor cell expansion and differentiation. Advantageously, the stiffness of the hydrogel can be repeatably and reversibly adjusted to modulate the growth and/or proliferation of cells provided within the hydrogel as well as the release of bioactive agents provided in the hydrogel from the hydrogel. Moreover, when hydrogel is used as a tissue, which is exposed to mechanical stresses (i.e., shear and tensile stresses) in in vivo environments, the mechanical properties of the hydrogel can be increased following secondary crosslinking to improve its stability when used in such applications.

The following example is for the purpose of illustration only and is not intended to limit the scope of the claims, which are appended hereto.

EXAMPLE

In this Example, we engineered a cell-laden hydrogel system with reversibly tunable stiffness using a dual-crosslinkable alginate hydrogel based on ionic crosslinking and photocrosslinking over a physiologically relevant range of hydrogel stiffness.

Methods

Synthesis of OMA

The dual-crosslinkable, biodegradable OMA was prepared by the oxidation and methacrylation of alginates.

Briefly, sodium alginate (10 g, Protanal LF 200S, FMC Biopolymer) was dissolved in ultrapure deionized water (diH$_2$O, 900 ml) overnight. Sodium periodate (0.1 g, Sigma) was dissolved in 100 ml diH$_2$O, added to alginate solution under stirring in the dark at room temperature and then allowed to react for 24 hrs. To synthesize OMA, 2-morpholinoethanesulfonic acid (MES, 19.52 g, Sigma) and NaCl (17.53 g) were directly added to an oxidized alginate (OA) solution (1 L), and the pH was adjusted to 6.5 with 5 N NaOH. N-hydroxysuccinimide (NHS, 2.12 g; Sigma) and 1-ethyl-3-(3-dimethylaminopropyl)-carbodiimide hydrochloride (EDC, 7.00 g; Sigma) (molar ratio of NHS:EDC=1:2) were added to the mixture to activate 20% of the carboxylic acid groups of the alginate. After 5 min, 2-aminoethyl methacrylate (AEMA, 3.04 g) (molar ratio of NHS:EDC:AEMA=1:2:1) was added to the product, and the reaction was maintained in the dark at room temperature (RT) for 24 hrs. The reaction mixture was precipitated with the addition of acetone in excess, dried in a fume hood, and rehydrated to a 1 w/v % solution in diH$_2$O for further purification. The OMA was purified by dialysis against diH$_2$O (MWCO 12000~14000, Spectrum Laboratories Inc.) for 3 days, treated with activated charcoal (5 g/L, 50-200 mesh, Fisher Scientific) for 30 min, filtered (0.22 µm filter) and lyophilized. To determine the levels of alginate oxidation and methacrylation, the OMAs were dissolved in deuterium oxide (D$_2$O, Sigma) to a 2 w/v %, and $^1$H-NMR spectra were recorded on a Varian Unity-300 (300 MHz) NMR spectrometer (Varian Inc.) using 3-(trimethylsilyl) propionic acid-d$_4$ sodium salt (0.05 w/v %) as an internal standard.

Fabrication of OMA Hydrogels and In Situ Dynamic Stiffness Tuning

OMA (1.5 w/v %) and CGGGRGDSP (10 mg/g OMA) were dissolved in Dulbecco's Modified Eagle Medium (DMEM, Sigma, St. Louis, MO) overnight with 0.05 w/v % photoinitiator [2-hydroxy-4'-(2-hydroxyethoxy)-2-methylpropiophenone, Sigma] at pH 7.4, placed between quartz (top) and glass (bottom) plates separated by 0.4 mm spacers, and then photocrosslinked with ultraviolet (UV) light (320-500 nm, EXFO OmniCure S1000-1B, Lumen Dynamics Group) at ~20 mW/cm$^2$ for 1 min to form a photocrosslinked hydrogel (Soft). Photocrosslinked hydrogel disks were created using an 8-mm diameter biopsy punch.

Photocrosslinked hydrogels were stiffened by incubating in 50 mM CaCl$_2$ for 10 min with gentle agitation, and then washed three times with DPBS (Stiff). To reversibly soften the hydrogels by removing calcium ions, Stiff hydrogels were incubated in Tris-EDTA (TE, 50 mM Tris, 5 mM EDTA, and pH 7.5) buffer for 10 min with gentle agitation, and then washed three times with DPBS.

Mechanical Testing

The elastic moduli of hydrogels were determined by performing uniaxial, unconfined constant strain rate compression testing at room temperature using a constant crosshead speed of 1%/sec on a mechanical testing machine (225 lbs Actuator, Test Resources) equipped with a 5 N load cell. Elastic moduli were calculated from the first non-zero linear slope of the stress versus strain plots.

Encapsulation of hMSCs and hASCs

To isolate hMSCs, bone marrow aspirates were obtained from the posterior iliac crest of a healthy twenty three-year old male donor under a protocol approved by the University Hospitals of Cleveland Institutional Review Board. The aspirates were washed with growth medium comprised of low-glucose Dulbecco's Modified Eagle's Medium (DMEM-LG, Sigma) with 10% prescreened fetal bovine serum (FBS, Gibco). Mononuclear cells were isolated by centrifugation in a Percoll (Sigma) density gradient and the isolated cells were plated at 1.8×10$^5$ cells/cm$^2$ in DMEM-LG containing 10% FBS, 1% penicillin/streptomycin (P/S, Thermo Fisher Scientific) and 10 ng/ml FGF-2 (R&D Systems) in an incubator at 37° C. and 5% CO$_2$. After 4 days of incubation, non-adherent cells were removed and adherent cell were maintained in DMEM-LG containing 10% FBS and 1% P/S with media changes every 3 days. After 14 days of culture, the cells were passaged at a density of 5×10$^3$ cells/cm$^2$.

hASCs were isolated from the adipose tissue. Lipoaspirates were digested with 200 unit/mg collagenase type I (Worthington Biochemical Products, Lakewood, NJ) for 40 min at 37° C. The stromal fraction was then isolated by density centrifugation and the stromal cells were plated at 3500 cell/cm$^2$ on tissue culture plastic in DMEM/nutrient mixture F12 (DMEM/F12, BioWhittaker, Suwance, GA) with 10% defined fetal bovine serum (FBS, HyClone, Logan, UT), 100 U/ml penicillin, 100 µg/ml streptomycin (1% P/S, BioWhittaker), and 10 ng/ml FGF-2 (R&D Systems).

OMA (1.5 w/v %) was dissolved in DMEM with a photoinitiator (2-Hydroxy-4'-(2-hydroxyethoxy)-2-methylpropiophenone, 0.05 w/v %, Sigma) at pH 7.4, and then hMSCs or hASCs (passage number 3, 2×10$^6$ cells/ml) were suspended in OMA solution. The cell suspension solution was placed between quartz (top) and glass (bottom) plates separated by 0.4 mm spacers and then photocrosslinked with UV light (320-500 NM, EXFO Omnicure® S1000-1B, Lumen Dynamics Group) at ~20 mW/cm$^2$ for 1 min to form photocrosslinked hydrogel-cell constructs (Soft). Hydrogel/cell-construct disks were created using an 8 mm diameter biopsy punch, placed in wells of 24-well tissue culture plates with 1 ml DMEM/F-12 containing 10% FBS, 1% P/S and 10 ng/ml FGF-2 and cultured in a humidified incubator at 37° C. with 5% CO$_2$. Soft hydrogel-cell constructs were stiffened by incubating in 50 mM CaCl$_2$ for 10 min with gentle agitation (Stiff), washed three times with DPBS, and then cultured in a humidified incubator at 37° C. with 5% CO$_2$. The stiffness of hydrogel-cell constructs was dynamically changed by incubating in TE (TE, 50 mM Tris, 5 mM EDTA, and pH 7.5) buffer for 10 min to remove calcium ions from stiff hydrogel-constructs or in CaCl$_2$ solution (50 mM Ca$^{2+}$) for 10 min to add calcium ions into soft hydrogel-constructs. All experimental groups were described in Table 1. The elastic moduli of hydrogel-constructs were determined as described above.

Cell Responses in Dynamically Tunable Hydrogels

The cell viability and morphology of encapsulated hMSCs and hASCs in the dynamically tunable hydrogels were investigated using Live/Dead staining comprised of fluorescein diacetate (FDA) and ethidium bromide (EB). The staining solution was freshly prepared by mixing 1 ml FDA solution (1.5 mg/ml in dimethyl sulfoxide, Sigma) and 0.5 ml EB solution (1 mg/ml in PBS, Thermo Fisher Scientific) with 0.3 ml PBS (pH 8). At predetermined time points, 20 µl of staining solution was added into each well and incubated for 3-5 min at room temperature, and then stained hydrogel-cell constructs were imaged using a fluorescence microscope (ECLIPSE TE 300) equipped with a digital camera (Retiga-SRV).

To quantify the roundness and cell area, image analysis was performed using ImageJ (NIH). To determine cellular domains, Otsu's intensity-based color thresholding method was applied to fluorescent images and binary masks was created for each cell. These binary masks were used to calculate cell roundness and spread area. The roundness of cells was calculated with the ratio of major axis to the minor axis.

To determine the effect of the hydrogel stiffness changes on cell growth, at predetermined time points, some hydrogel-cell constructs were removed from the 24-well plates, put in 1 ml cell lysis buffer (Sigma) and homogenized at 35,000 rpm for 30 seconds using a TH homogenizer (Omni International). The homogenized solutions were centrifuged at 500 g with a Sorvall Legent RT Plus Centrifuge (Thermo Fisher Scientific). The supernatants were collected for DNA analysis. DNA content in supernatant was measured using a Picogreen assay kit (Invitrogen) according to the manufacturer's instructions. Fluorescence intensity of the dye-conjugated DNA solution was measured using a fluorescence microplate reader (FMAX, Molecular Devices) set at 485 nm excitation and 538 nm emission.

Results

Figure 1:
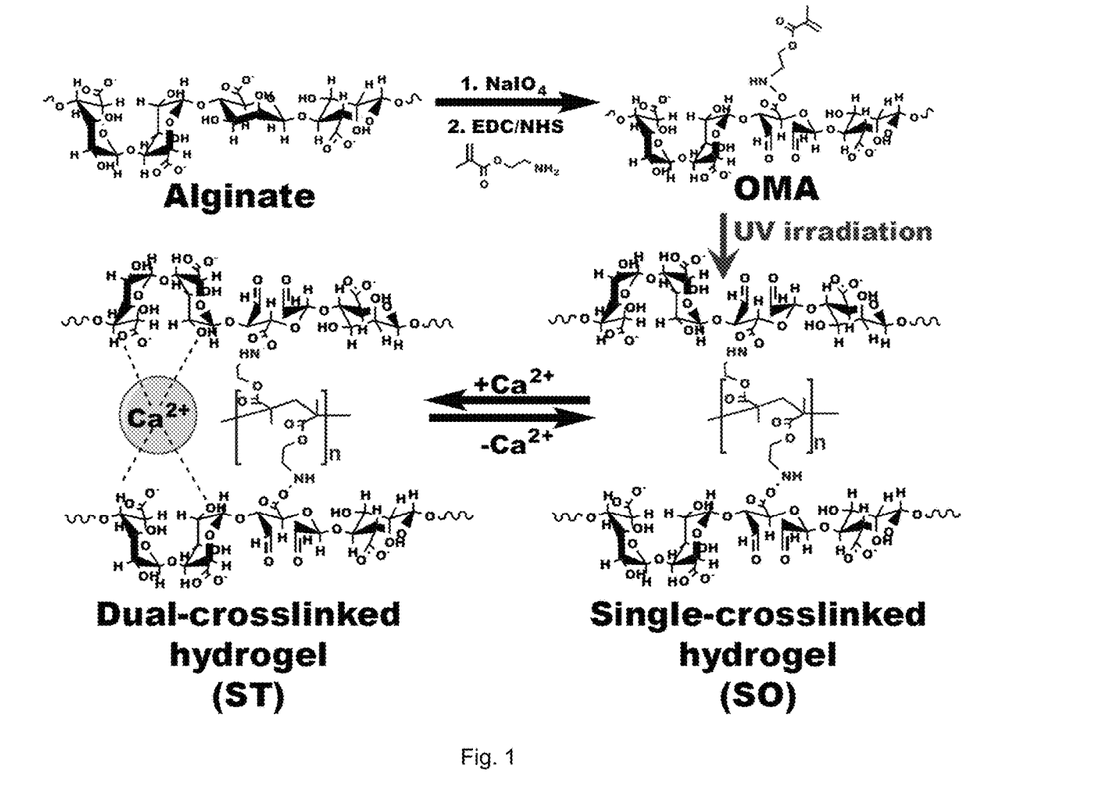
FIG. 1 is a schematic illustration of the preparation and chemical structures of OMA, single-crosslinked soft (SO) and dual-crosslinked stiff (ST) hydrogels.

The overall strategy for the formation of the dynamically tunable alginate hydrogels is depicted in FIG. 1. Oxidized methacrylated alginate (OMA) was prepared by functionalizing alginate through both oxidation and methacrylation to enhance the hydrolytic degradation and to form a dual-crosslinkable alginate hydrogel, respectively. The primary single-crosslinked hydrogel network (Soft) was formed by photopolymerization of the methacrylate groups of OMAs. To generate a dual-crosslinked hydrogel (Stiff), a second crosslinked network was formed by ionic crosslinking of the single-crosslinked alginate hydrogel. The guluronic acids across different alginates can form ionic crosslinks with $Ca^{2+}$, resulting in a dual-crosslinked hydrogel network.

Figure 2A:
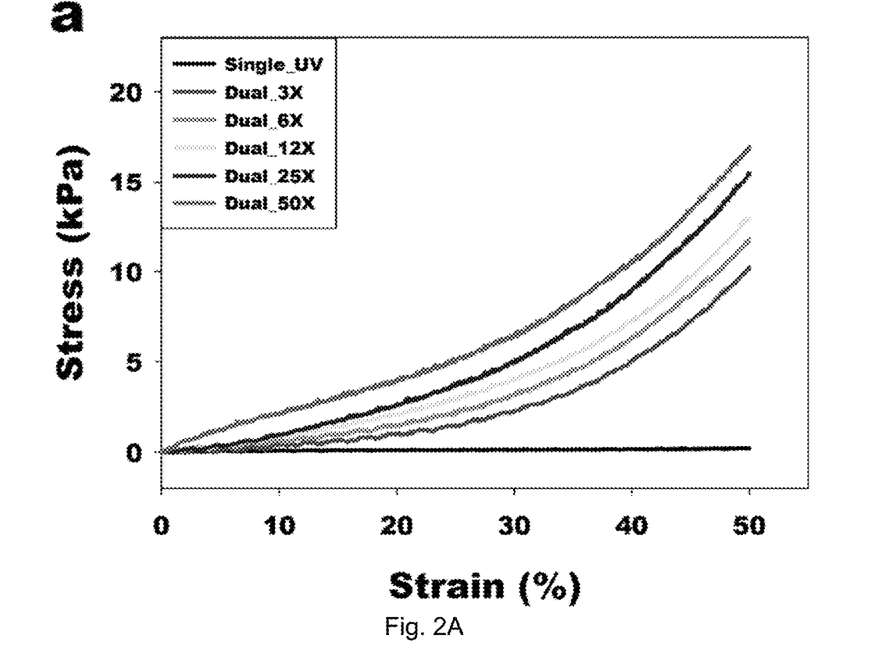
FIGS. 2A-C illustrate (A) representative stress-strain curves and (B) compressive modulus of hydrogels. The addition of $Ca^{2+}$ led to stiffening of the single-crosslinked SO hydrogel (Single_UV) with various concentration of $Ca^{2+}$ [3.125 mM (3×), 6.25 mM (6×), 12.4 mM (12×), 25 mM (25×) and 50 mM (50×)]. Compressive modulus was calculated within 5% strain. (C) Dynamic reversible tuning of hydrogel stiffness. Modulus changes and proposed structures of reversibly tunable hydrogels. To stiffen the hydrogels, SO hydrogels were incubated in 50× $Ca^{2+}$ solution for 10 min. To soften the hydrogels, ST hydrogels were incubated in 5× TE buffer (50 mM Tris and 5 mM EDTA at pH 7.5) for 10 min. Compressive modulus of hydrogels was calculated using stress-strain curves within 5% strain. Quantitative data are expressed as means±standard deviations. Statistical analysis was performed by one-way analysis of variance (ANOVA) with the Tukey significant difference post hoc test using Origin software (OriginLab Co., Northampton, MA). A value of $p<0.05$ was considered statistically significant.
Figure 2B:
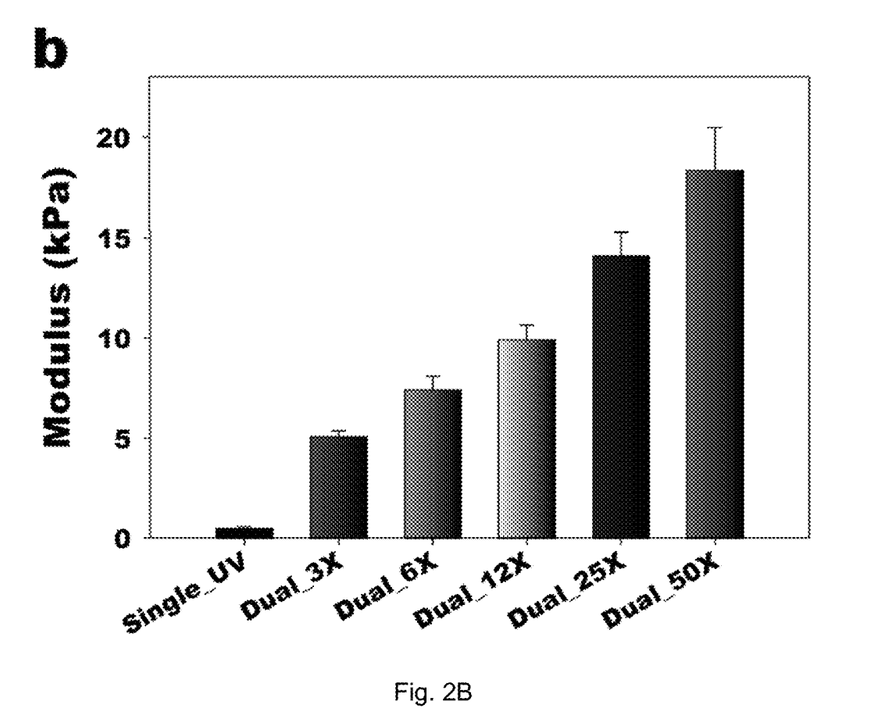
Figure 2C:
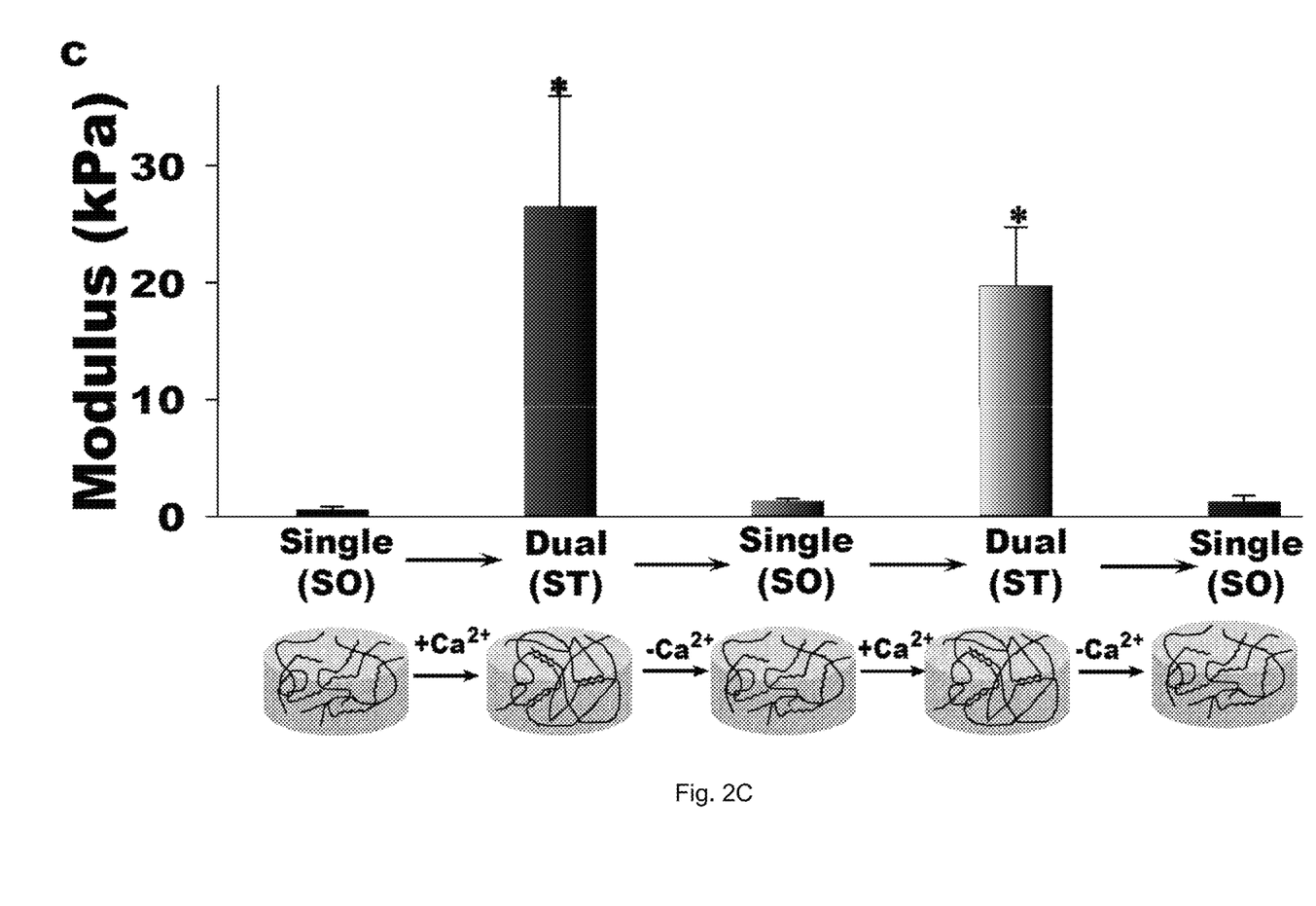

In situ, on-demand hydrogel stiffening was confirmed by measuring the elastic modulus of OMA hydrogels after forming dual-crosslinked networks by incubating in $Ca^{2+}$-containing solutions. The addition of $Ca^{2+}$ led to stiffening of the single-crosslinked hydrogel (Single_UV; Soft) (FIG. 2A). The dynamic elastic modulus range of the represented hydrogels spans approximately up to 20 kPa by varying the amount of $Ca^{2+}$ (FIG. 2B). The elastic modulus of the single-crosslinked OMA hydrogels (Single_UV) was 0.52±0.04 kPa (FIG. 2B). As the concentration of $Ca^{2+}$ increased from 3.125 mM (3×) to 50 mM (50×), the elastic moduli of OMA hydrogels were increased from 5.11±0.25 kPa to 18.37±2.13 kPa (FIG. 2B), indicating an ability to manipulate hydrogel stiffness by changing the concentration of $Ca^{2+}$. To demonstrate the dynamic and reversible mechanical property changes of hydrogels, the single-crosslinked (Soft) hydrogel was first incubated in a 50 mM $Ca^{2+}$ solution. The modulus of the hydrogel was increased from 0.57±0.25 kPa (black bar) to 26.52±9.47 (red bar) kPa within 10 min (FIG. 2C). When the stiffened hydrogel was incubated in Tris-ethylenediamine tetraacetic acid (TE) buffer solution for 10 min to remove $Ca^{2+}$, the modulus of hydrogel was decreased to 1.29±0.19 kPa (green bar). The modulus of this softened hydrogel was further increased to 20±0.19 kPa by incubating in a 50 mM $Ca^{2+}$ solution for 10 min (yellow bar). Subsequent hydrogel softening was also achieved by removing $Ca^{2+}$ ions from the stiffened hydrogel by incubating in TE buffer solution (blue bar). This result demonstrated a unique strategy for on-demand, dynamic and reversible control of hydrogel mechanics by single and dual-crosslinking mechanism.

While numerous studies have investigated the cellular response to static matrix stiffness on 2D and in 3D matrices, there are only few reports on the effect of dynamic mechanical cues on encapsulated cells in biomaterials. Thus, to demonstrate whether this hydrogel system could be used to apply reversible mechanical signals on 3D encapsulated cells, human mesenchymal stem cells (hMSCs) derived from bone marrow were photoencapsulated in single-crosslinked (SO) or dual-crosslinked (ST) OMA hydrogels, then the stiffnesses of the hydrogel constructs were decreased or increased every week by removing or adding $Ca^{2+}$, respectively.

Figure 3A:
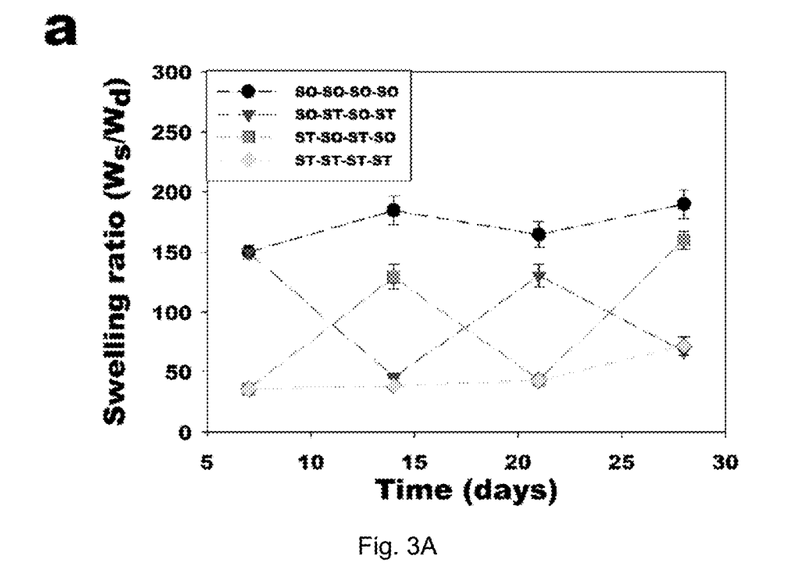
FIGS. 3A-C illustrate plots showing characteristics of dynamically tunable hydrogels. (A) Swelling ratios and (B) mass loss of hydrogels without cells in DMEM over time. Encapsulation of hMSCs in the hydrogels. (C) Elastic modulus changes of hMSC encapsulated hydrogel constructs in growth media over time.
Figure 3B:
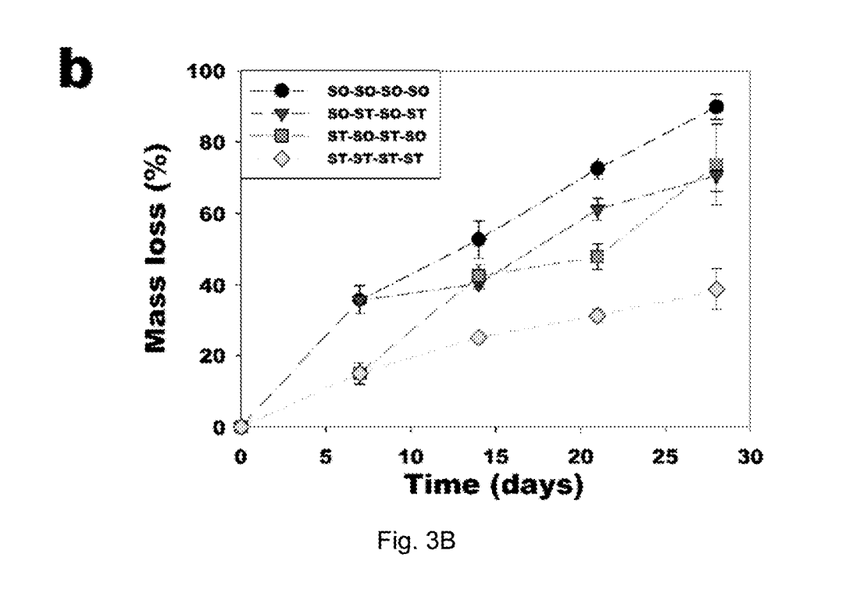
Figure 3C:
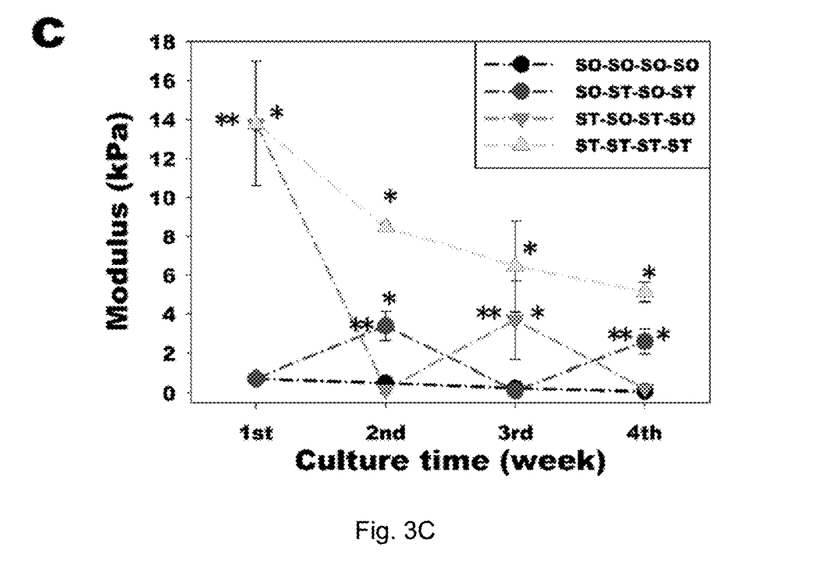

As shown in FIG. 3a, the swelling ratio of the static SO hydrogels (SO-SO-SO-SO) was significantly higher than that of the static ST hydrogels (ST-ST-ST-ST) for 4 weeks while the swelling ratio of both groups stayed relatively constant. However, SO-ST-SO-ST and ST-SO-ST-SO hydrogels exhibited the dynamic swelling kinetics. When the hydrogels were stiffened by adding $Ca^{2+}$, the swelling ratio of hydrogels was decreased. This decreased swelling ratio of hydrogels could be increased by removing $Ca^{2+}$ and thus softening them. The mass loss of hydrogels over time was determined as a measure of degradation (FIG. 3B). Compared to the static ST hydrogels (ST-ST-ST-ST), the static SO hydrogels (SO-SO-SO-SO) exhibited faster degradation. Similar to the swelling ratio changes, the degradation rate of hydrogels was decreased when the hydrogels were stiffened by adding $Ca^{2+}$. This decreased degradation rate could be increased by softening of hydrogels.

Although the moduli of hydrogels were continuously decreased as hydrogels degraded, the moduli of hydrogels could be significantly changed every week (FIG. 3A). The modulus of the static ST hydrogels (ST-ST-ST-ST) was significantly higher than that of the SO hydrogels (SO-SO-SO-SO) for 4 weeks. The moduli of both hydrogel groups gradually decreased as the hydrogels degraded. The elastic moduli of ST hydrogels (ST-ST-ST-ST) significantly decreased to 0.18±0.16 kPa when incubated in TE buffer at the $2^{nd}$ week (ST-SO-ST-SO). When the in situ softened constructs were incubated in $Ca^{2+}$ solution at the $3^{rd}$ week, the hydrogels could be stiffened again (3.60±2.02 kPa). Similar to the initial ST constructs, the moduli of SO constructs (SO-SO-SO-SO) significantly increased to 3.37±0.75 kPa (SO-ST-SO-ST) by incubating in $Ca^{2+}$ solution at the $2^{nd}$ week. When the in situ stiffened constructs were incubated in TE buffer at the $3^{rd}$ week, the constructs were softened again (0.12±0.16 kPa). These stiffened or softened hydrogels could be softened or stiffened by removing or adding $Ca^{2+}$, demonstrating the process of stiffening/softening was reversible and repeatable.

To investigate the effect of hydrogel stiffness changes on the viability and morphology of encapsulated hMSCs, we changed the stiffness of hydrogel constructs every week and performed Live/Dead staining. As shown in FIG. 3A, high cell viability was observed throughout all groups for 4 weeks, indicating the encapsulation process, the macromers and their degradation products and the stiffening and softening of hydrogel constructs were all cytocompatible. The fluorescence photomicrographs showed that almost all of the hMSCs encapsulated in the static ST hydrogels displayed a rounded morphology for 4 weeks. In contrast, hMSCs encapsulated in the static SO hydrogels demonstrated cell spreading at the $1^{st}$ week and continuously spread for 4 weeks. When the SO hydrogel construct was stiffened at the $1^{st}$ week and cultured for another week (SO-ST), the morphology of hMSCs was rounded, though the hMSC spread was much greater than in the static SO hydrogels. The rounded morphology of hMSCs in the stiffened hydrogels (SO-ST) changed significantly in the $3^{rd}$ week to a spread morphology in response to softening hydrogels at the $2^{nd}$ week (SO-ST-SO). Similar to the morphology changes of the hMSCs in the $2^{nd}$ week, the spread morphology of the hMSCs in the softened hydrogels rounded again by stiffening the hydrogel constructs (SO-ST-SO-ST). When the Stiff hydrogel constructs were softened at the $1^{st}$ week and cultured for another week (ST-SO), the hMSCs started spreading, whereas the hMSCs remained rounded in the static Stiff hydrogel constructs. The spread morphology of the hMSCs in the softened hydrogels (ST-SO) changed to a rounded morphology in the $3^{rd}$ week by stiffening the hydrogel constructs (ST-SO-ST). This rounded morphology of the hMSCs in the stiffened hydrogel constructs could be also changed to a spread morphology by softening the hydrogel constructs (ST-SO-ST-SO). We also confirmed these results by the quantification of roundness of hMSCs (FIG. 3B). Cell spread area was also assess for each stiffness condition. As the stiffness of the hydrogel constructs was decreased, cell area increased. Upon stiffening the hydrogel constructs, cell area decreased again. These data indicate the mechanics of hydrogels significantly change the morphology of encapsulated cells, and the hMSCs sense the change of mechanics in situ. Similar to the hMSCs, the spreading and proliferation of human adipose tissue-derived stromal cells (hASCs) were also controllable by regulating the stiffness of hydrogels.

Figure 4A:
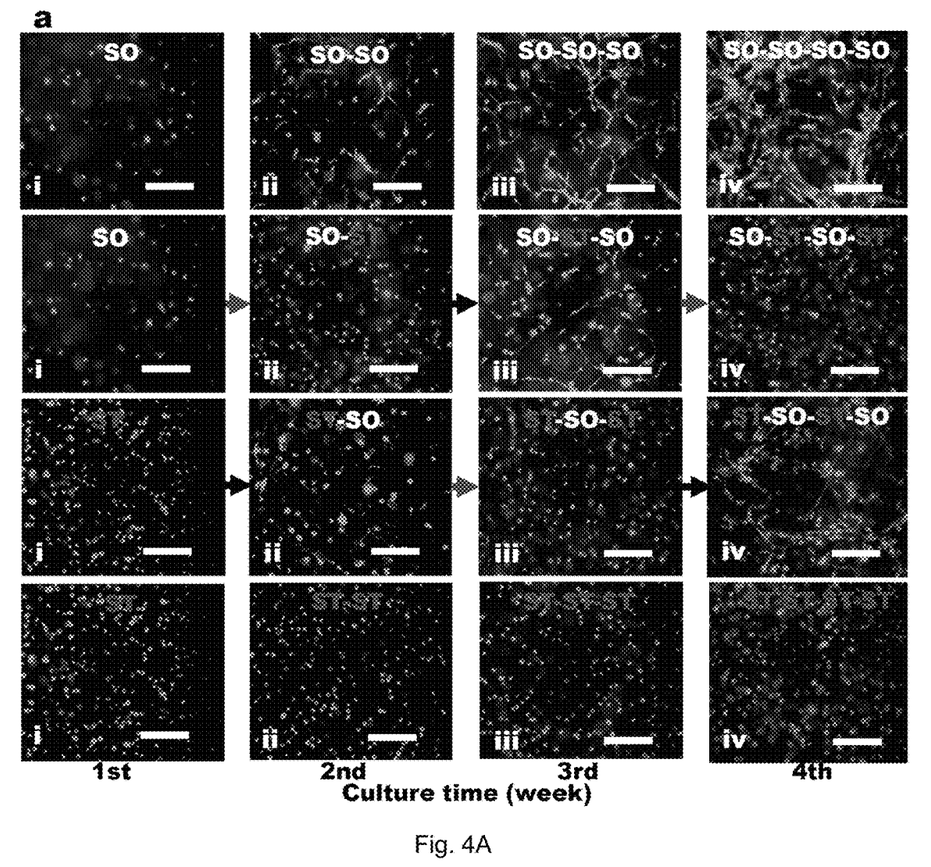
FIGS. 4A-D illustrate photomicrographs and graphs showing hMSC response on reversible dynamic mechanics in 3D. (A) Representative live and dead photomicrographs of encapsulated hMSCs in the hydrogels for 4 weeks. Grey arrows mean stiffening of hydrogels and black arrows mean softening of hydrogels. The scale bars indicate 100 µm. Quantification of (B) roundness and (C) cell area in hydrogels. (D) Quantification of DNA contents in hMSC encapsulated hydrogels over time. Quantitative data are expressed as means±standard deviations. Statistical analysis was performed by one-way ANOVA with the Tukey significant difference post hoc test using Origin software. A value of $p<0.05$ was considered statistically significant.
Figure 4B:
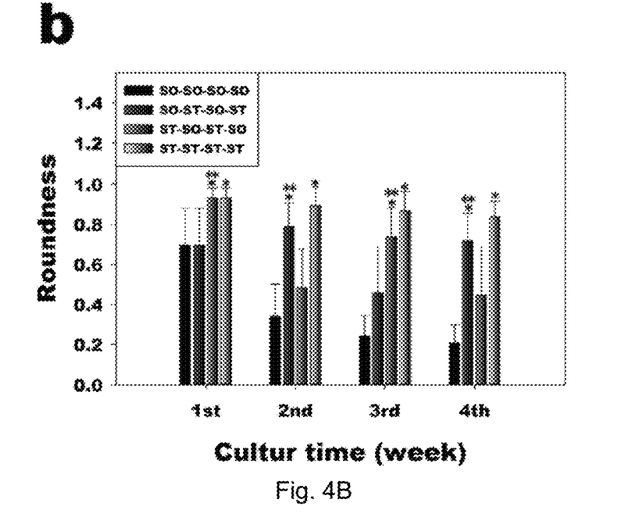
Figure 4C:
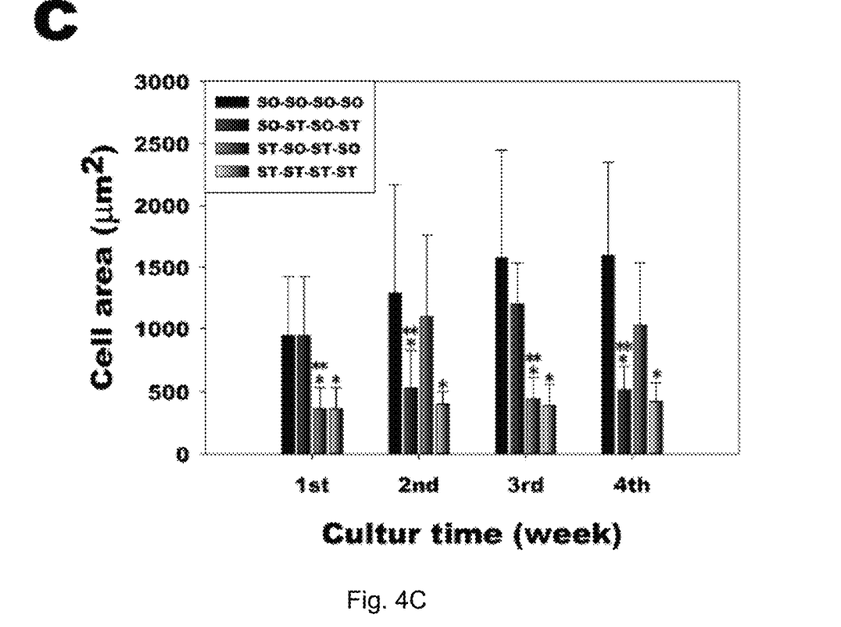
Figure 4D:
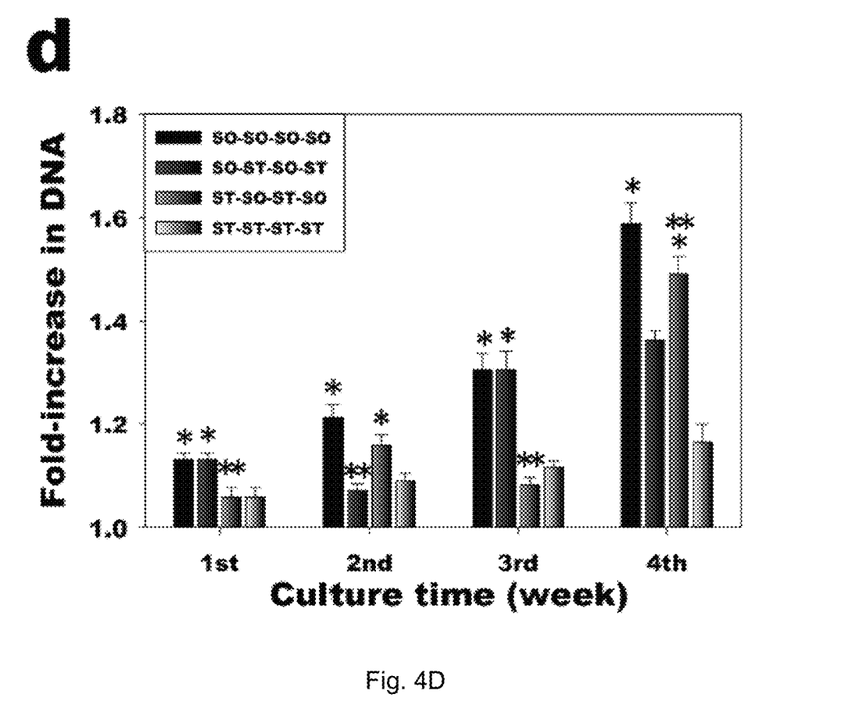

To evaluate the effect of hydrogel stiffness changes on the growth of the encapsulated hMSCs, we measured the DNA content in the hydrogel constructs every week. As shown in FIG. 4D, the hMSCs encapsulated in the static hydrogels continuously grew for 4 weeks as determined by a DNA content assay while the proliferation rate of hMSCs encapsulated in the static SO hydrogels (SO-SO-SO-SO) was significantly higher than that of hMSCs in the static ST hydrogels (ST-ST-ST-ST). Importantly, the proliferation rate of hMSCs encapsulated in the Soft hydrogels decreased when the hydrogel constructs were stiffened at the $1^{st}$ week (SO-ST-SO-ST). When the stiffened hydrogel constructs were softened again by removing $Ca^{2+}$ the $2^{nd}$ week, the decreased proliferation rate of the encapsulated hMSCs recovered. Similar to the SO hydrogel constructs, the proliferation rate of hMSCs encapsulated in the ST hydrogels could increase by softening the hydrogel constructs by the softening at 1st week (ST-SO-ST-SO). Subsequent hydrogel constructs stiffening decreased this increased proliferation rate of encapsulated hMSCs. These results demonstrated that the growth of encapsulated hMSCs was reversibly and repeatedly controllable by stiffening or softening the hydrogel constructs.

In conclusion, this example demonstrates a strategy for on-demand, reversible dynamic control of hydrogel mechanics with OMAs via dual-crosslinking mechanism. The moduli limits of hydrogels are tunable by varying the second crosslinking density. By showing response in hMSC proliferation and morphology changes to dynamic mechanics of hydrogels, reversible 3D cellular mechanosensing also has been demonstrated. This system provides a powerful tool with a wider range of stiffness tunability to investigate dynamic changes in mechanobiology, biological processes and tissue development.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

Having described the invention, we claim:

1. A composition comprising: a dual crosslinkable hydrogel that comprises a plurality of polymer macromers that are crosslinked with a first agent and a second agent different than the first agent, wherein the polymer macromers are ionically crosslinkable with the second agent and the crosslinks formed using the second agent are reversible and repeatable to allow the mechanical properties of the hydrogel to be dynamically adjusted by increasing or decreasing crosslinking with the second agent.

2. The composition of claim 1, wherein the stiffness of the hydrogel is dynamically adjusted by increasing or decreasing crosslinking with the second agent.

3. The composition of claim 1, wherein an increase of the crosslinks formed using the second agent increases the stiffness of the hydrogel and a decrease in the crosslinks formed using the second agent decreases the stiffness of the hydrogel.

4. The composition of claim 1, further comprising at least one bioactive agent.

5. The composition of claim 4, wherein release of the bioactive agent from the hydrogel is controlled by dynamically adjusting the mechanical properties of the hydrogel.

6. The composition of claim 1, further comprising a plurality of cells dispersed on and/or within the hydrogel.

7. The composition of claim 6, wherein growth and/or proliferation of the cells within the hydrogel is controlled by dynamically adjusting the mechanical properties of the hydrogel.

8. The composition of claim 1, wherein the polymer macromers comprise biodegradable acrylated and/or methacrylated natural polymer macromers.

9. The composition of claim 8, wherein the acrylated and/or methacrylated, natural polymer macromers are polysaccharides, which are optionally oxidized.

10. The composition of claim 8, the natural polymer macromers comprising oxidized, acrylated and/or methacrylated alginates.

11. The composition of claim 1, wherein the polymer macromers are photocrosslinkable with the first agent.

12. The composition of claim 1, wherein second agent comprises calcium ions.

* * * * *